United States Patent [19]

de Vincentiis

[11] 4,440,787
[45] Apr. 3, 1984

[54] COMPOUNDS WITH ANTIINFLAMMATORY AND ANALGESIC ACTIVITY, PROCESS FOR THE PREPARATION THEREOF AND PHARMACEUTICAL COMPOSITIONS THEREFROM

[75] Inventor: Leonardo de Vincentiis, Rome, Italy

[73] Assignee: Ausonia Farmaceutici s.r.l., Pomezia, Italy

[21] Appl. No.: 380,125

[22] Filed: May 20, 1982

[30] Foreign Application Priority Data

Nov. 24, 1981 [IT] Italy ................................ 25243 A/81

[51] Int. Cl.$^3$ ....................... C07C 59/52; A01N 37/12
[52] U.S. Cl. .................................... 424/319; 424/316; 562/569; 260/501.11; 260/501.14; 260/501.17
[58] Field of Search ................ 424/319, 316; 562/569; 260/501.11, 501.14, 501.17

[56] References Cited

U.S. PATENT DOCUMENTS

| 3,755,603 | 8/1973 | Harrison et al. | 562/469 |
| 3,948,973 | 4/1976 | Phillips | 562/469 |
| 4,021,479 | 5/1977 | Seeger et al. | 562/469 |
| 4,151,302 | 4/1979 | Ganto et al. | 562/469 |
| 4,188,491 | 2/1980 | Nicholson et al. | 562/469 |
| 4,189,499 | 2/1980 | Tosi et al. | 260/501.11 |
| 4,225,730 | 9/1980 | Jones et al. | 562/469 |
| 4,278,678 | 7/1981 | Hamazaki et al. | 562/469 |

Primary Examiner—James H. Reamer
Attorney, Agent, or Firm—Bucknam and Archer

[57] ABSTRACT

The compound (2′,4′-difluoro-4-biphenyl)oxypropionic acid and its pharmaceutically acceptable salts with a metal or an organic base are described. They exhibit high antiinflammatory and analgesic activity and do not cause gastric lesions.

10 Claims, No Drawings

COMPOUNDS WITH ANTIINFLAMMATORY AND ANALGESIC ACTIVITY, PROCESS FOR THE PREPARATION THEREOF AND PHARMACEUTICAL COMPOSITIONS THEREFROM

The present invention relates to substituted oxypropionic acids and more specifically to novel compounds exhibiting high antiinflammatory activity, high analgesic activity and free from gastric lesion effects. The novel compounds according to the present invention are represented by the compound (2',4'-difluoro-4-biphenyl)oxypropionic acid of formula I:

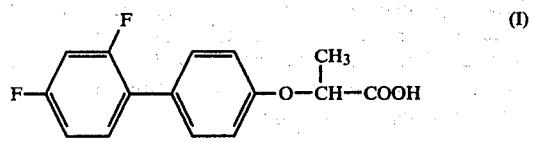

and its pharmaceutically acceptable salts with metallic ions, such as sodium, potassium, magnesium, and calcium or with pharmaceutically acceptable organic bases, such as lysine, arginine, diethanolamine. An object of the present invention is to prepare novel compounds exhibiting high antiinflammatory activity and analgesic activity and completely free of gastric lesion effects. Another object of the present invention is to provide a process for the preparation of the acid of formula I and its salts. Still another object of the present invention is to provide pharmaceutical compositions and a method of administration of the novel compounds according to the present invention. The process of preparation of the compound of formula I consists of reacting the sodium salt of 4-(2',4'-difluorophenyl)phenol II with ethylbromopropionate III, obtaining the ester of formula IV and hydrolyzing the ester in accordance with the reaction scheme hereinbelow:

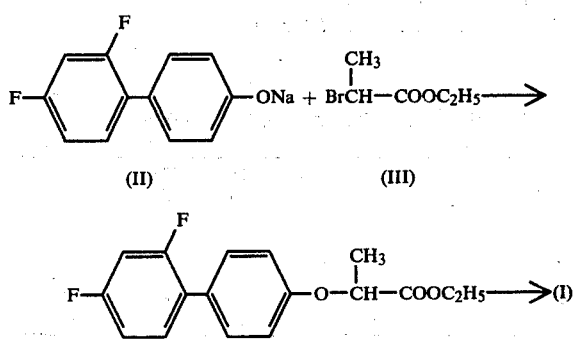

The reaction between compound II and compound III may be carried out in a lower alcohol, preferably ethanol, the compound of formula II being advantageously prepared in situ. The ester of formula IV may be hydrolyzed directly in the crude state with an aqueous solution of an alkali hydroxide. From the solution of the salt of the compound of formula I, the acid of formula I is obtained by acidification with an inorganic acid.

EXAMPLE I

Method of Preparation

In a flask of 100 cc capacity, sodium in the amount of 0.22 grams is reacted with 30 cc of absolute ethanol. After the sodium has completely gone in solution, there are added 2 grams of 4-(2',4'-difluorophenyl)phenol and then 1.5 cc of ethylbromopropionate. The mixture is allowed to reflux for four hours and then the solvent is evaporated on the vacuum. The residue is treated with 30 cc of 10% sodium hydroxide and allowed to reflux for three hours. After cooling, the solution is acidified with dilute hydrochloric acid. The precipitate is filtered with suction and recrystallized from a mixture of ethyl ether-n-hexane. Yield: 1.9 grams of the acid of formula I (74%). The acid melts at 153°–155° C. It is soluble in hot lower alcohols, insoluble in chlorinated hydrocarbons and essentially insoluble in water.

Elementary Analysis

Calcd for $C_{15}H_{12}F_2O_3$ (mol. wt.=278.24) Calcd.%: C=64.74; H=4.35 Found %: C=64.69; H=4.38

Spectrum IR (nujol mull): 1600 cm$^{-1}$, 1705 cm$^{-1}$, 1715 cm$^{-1}$;

Spectrum H$^1$ NMR (determined in DMSO hexadeuterated, internal reference TMS): 1.55 δ(d, 3H, CH$_3$); 4.85 δ(9, 1H, O—CH—); 6.8-7.7 δ(m, 7H aromatic, 1H mobile).

The acid of formula I will be referred hereinbelow with the symbol MR 714. The acid is used to prepare the salts in a conventional manner. The examples which follow illustrate the preparation and the properties of some salts of the acid of formula I, but are not intended to be limitative of the invention.

EXAMPLE 2

To a warm solution of 25 grams (90 mmoles) of (2',4'-difluoro-4-biphenyl)oxypropionic acid (I) in 250 cc of ethanol, there are added 4.86 grams (90 mmoles) of pure sodium methoxide. A crystalline solid is formed even in the hot solution and the precipitation is completed by cooling. After recrystallization from water, there are obtained 22 grams of the sodium salt of the compound of formula I; melting point 258°–261° C. (dec.).

EXAMPLE 3

To a warm solution of 50 grams (180 mmoles) of compound (I) and 15 g (180 mmoles) of NaHCO$_3$ in 300 cc of water, there is added a hot aqueous solution of 10.7 grams (90 mmoles) of calcium chloride in 80 cc of water. By cooling, a crystalline solid precipitates the analytical data of which agree with the following formula:

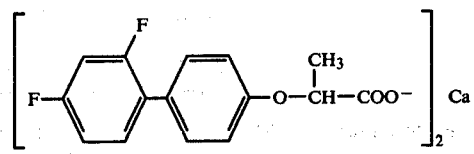

The substance melts with decomposition above 286° C.

Infrared Spectrum-(nujol mull): 1045 cm$^{-1}$, 1250 cm$^{-1}$, 1590 cm$^{-1}$, 1600 cm$^{-1}$.

Spectrum H$^1$ NMR (determined in DMSO hexadeuterated, internal reference TMS; the values of chemical shifts are given in δ): 1.5 (d, 3H, CH—CH$_3$); 4.5 (q, 1H, CH—CH$_3$); 6.7-7.5 (m, 7H aromatic).

EXAMPLE 4

The acid of formula I, 50 grams (90 mmoles), is dissolved by warming in 250 cc of ethyl acetate; 11 grams (90 mmoles) of ethanolamine is added. The salt which precipitates partially, even from the warm solution, is isolated by filtration and washed on the filter paper first with ethyl acetate and then with diethyl ether. A crystalline solid, in the amount of 57 grams, is obtained, melting point 125°-127° C.

Elementary Analysis Calcd. for $C_{17}H_{19}F_2NO_4$ (Mol. Wt.=339.33) Calcd. %: C=56.63; H=5.70; N=4.13 Found %: C=56.56; H=5.78; N=4.02.

Infrared Spectrum (nujol mull): 1050 cm$^{-1}$ (sym. stretch C—O), 1235 cm$^{-1}$ (asym. stretch C=C), 1610 cm$^{-1}$ (stretch C=O), 2750-2600 cm$^{-1}$ (stretch N$^+$—H), 3450-3200 cm$^{-1}$ (stretch O—H).

H$^1$ NMR Spectrum (determined in CDCl$_3$/(CD$_3$)$_2$SO 50:50, internal reference TMS): 1.5 δ(d, 3H, CH—CH$_3$); 2.7-3 δ(t, 2H, CH$_2$—NH$_2$); 3.5-3.7 δ(t, 2H, CH$_2$—OH); 4.5 δ(q, 1H, CH—CH$_3$); 6.5-7.3 δ(m, 11H, aromatic 7H and mobile 4H).

EXAMPLE 5

In analogy with Example 4, but using L-lysine, instead of ethanolamine as the starting material, there is obtained the corresponding salt of L-lysine, melting point 193°-196° C.

Elementary Analysis Calcd. for $C_{21}H_{26}F_2N_2O_5$ (Mol. Wt.=424.43) Calcd. %: C=59.42; H=6.17; N=6.60 Found %: C=59.38; H=6.23; N=6.44

Analgesic Activity

The analgesic activity has been tested in mice using the contorsion test caused by phenylquinone. MR 714 has been administered by the oral route in the dose of 25 mg/kg. 30 minutes before phenylquinone. The substances used for comparison purposes have been acetyl salicylic acid, ibuprofen, paracetamol (p-acetylaminophenol) and diflunisal in the doses reported in Table I. The results obtained, reported in Table 7, show that MR 714, in the adopted experimental conditions, is endowed with a high analgesic activity, which is essentially the same as diflunisal, is substantially superior to paracetamol even when the latter is used in doses four times larger, and is essentially equivalent to the activity of acetylsalicylic acid, and of ibuprofen, respectively being employed in doses four times and ten times larger.

Antiinflammatory Activity

The experiments have been carried out with rats by administering MR 714 by oral route in the dose of 25 mg/kg. The substances which are used for comparison purposes have been acetylsalicylic acid, ibuprofen, paracetamol and diflunisal. 30 Minutes after the administration of the drugs, the right paw of the animals was made edematous by means of carrageenine subplantar injection; the volume of the inflamed limb was subsequently recorded, every hour, for the following 5 hours. The obtained results reported in Table II clearly show the considerable antiinflammatory activity of MR 714.

Gastric Tolerability

Considering the well-known reactions of the gastric mucosa towards most of the anti-inflammatory, non-steroid agents, the evaluation of the effects of MR 714 was thought to be necessary also in this respect. Rats kept fasting for a period of eighteen hours have been administered by the oral route with MR 714 and, for comparison purposes, with acetylsalycilic acid, ibuprofen, paracetamol and diflunisal. The doses employed and the results obtained are shown in Table III. From these experiments, it derives clearly that MR 714 is perfectly tolerated by the gastric mucosa, that was examined 6 hours after the treatment. It virtually causes non gastric lesions, and even less lesions as compared with the comparison drugs.

Acute Toxicity

MR 714 presents a very low acute toxicity: Its DL$_{50}$ in mice by the oral route is 840 mg/kg of body weight.

TABLE I

| | ANALGESIC ACTIVITY | | | |
|---|---|---|---|---|
| Treatment | Dose mg/kg/os | Average No. of Contorsions | % Inhibition vs. Controls | No. of Animals with Contorsions |
| Control | | 23.5 ± 6.1 | | 10/10 |
| Acetyl Salycilic Acid | 250 | 0 | 100 | 0/10 |
| Ibuprofen | 100 | 0.2 ± 0.1 | 99.1 | 2/10 |
| Paracetamol | 100 | 8.6 ± 3.3 | 63.4 | 5/10 |
| Diflunisal | 25 | 0.2 ± 0.2 | 99.1 | 1/9 |
| MR 714 | 25 | 0.2 ± 0.2 | 99.1 | 1/9 |

TABLE II

ANTIINFLAMMATORY ACTIVITY
Subplantar Edema Caused by Carrageenan in Rats

| Substance | Dose mg/kg/os | Volume of Paw in No. of Hours after the Treatment | | | | | | AREA | |
|---|---|---|---|---|---|---|---|---|---|
| | | 0 | 1 | 2 | 3 | 4 | 5 | Absolute Value | % Inhibition vs. Control |
| Controls | — | 21.3 | 28.1 | 34.9 | 38.2 | 37.3 | 32.6 | 273.2 | — |
| Acetyl-Salicyclic Acid | 250 | 20.0 | 23.6 | 28.0 | 29.5 | 30.5 | 31.4 | 182.4 | 33.0 |
| Ibuprofen | 100 | 20.3 | 25.2 | 26.5 | 28.7 | 29.6 | 29.9 | 163.7 | 40.0 |
| Paracetamol | 100 | 20.4 | 25.2 | 31.9 | 34.9 | 33.9 | 32.7 | 245.7 | 10.0 |
| Diflunisal | 25 | 21.2 | 25.6 | 29.7 | 31.0 | 33.4 | 33.1 | 190.7 | 30.0 |
| MR 714 | 25 | 20.5 | 25.0 | 30.4 | 33.2 | 32.7 | 32.4 | 218.2 | 20.0 |

TABLE III

| GASTRIC LESION ACTIVITY | | |
|---|---|---|
| Treatment | Dose mg/kg/os | Average Size of Ulcer in mm |
| Controls | — | 0 |
| Acetyl Salicylic Acid | 250 | 3.7 ± 0.8 |
| Ibuprofen | 100 | 2.3 ± 0.7 |
| Paracetamol | 100 | 0.6 ± 0.4 |
| Diflunisal | 25 | 0.7 ± 0.4 |
| MR 714 | 25 | 0.1 ± 0.1 |

Pharmacokynetic and Metabolism

The tests have been carried out in rats, administering MR 714 by the oral route in the doses of 25, 50, and 100 mg/kg. After the treatment, the plasmatic levels rapidly increase, reaching a first peak between the fourth and the sixth hours; they subsequently decrease before rising towards a second, long-lasting, plateau peak that lasts until the 24th hour for the two higher doses, whereas it lasts a short time for the low dose. The half-life time of plasmatic levels is well calculated in the dose of 25 mg/kg, whereas it is not possible to calculate it with the two higher doses, because the plateau concerning the second peak lasts a long time. The dominating medium-life resulted to be of 13 hours, which is one of the highest values as compared with the anti-inflammatory non-steroid drugs, as regards to the examined species; in particular, this medium-life is more than two times higher (when the dose is the same) than the medium-life of diflunisal, and therefore it allows only one daily administration of MR 714. The concentrations on liver, kidneys, lungs and uterus did not result to be much unlike among them, and they resulted to be lower as compared with the plasmatic concentrations. Nevertheless, the ratio between the plasmatic and the uterine concentrations resulted to be 0.34, which is a particularly high value. The present invention also covers all the industrial applications and use of MR 714 and its salts as antiinflammatory and analgesic agents. A substantial aspect of the invention resides in pharmaceutical formulations which contain predetermined amounts of MR 714 or its salts. The compositions according to the present invention may be administered by the oral or parenteral route, for instance in the form of compresses, capsules, powders, which may be dispersed in water and packaged in small envelopes, phthials suitable for injection. By way of example, the following formulations may be used:

(a) compresses containing 250 mg of (2′,4′-difluoro-4-biphenyl)oxypropionic acid with excipients and dispersing agents conventionally used in the pharmaceutical industry;

(b) compresses containing 375 mg of the acid of formula I containing the additional excipients and dispersing agents as above;

(c) phthials containing 400 mg of the lysine salt of (2′,4′-difluoro-4-diphenyl)oxypropionic acid which has been lyophilized, together with a phthial of about 3 cc of solvent for intramuscular injection.

I claim:

1. The compound (2′,4′-difluoro-4-biphenyl)oxypropionic acid of formula I

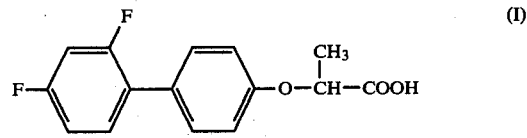

or a pharmaceutically acceptable salt thereof with a metal which is sodium, potassium, calcium or magnesium or an organic base which is lysine, arginine or ethanolamine.

2. The compound according to claim 1, which is the sodium salt of said acid of formula I.

3. The compound according to claim 1, which is the calcium salt of said acid of formula I.

4. The compound according to claim 1, which is the lysine salt of said acid of formula I.

5. The compound according to claim 1, which is the arginine salt of said acid of formula I.

6. The compound according to claim 1, which is the ethanolamine salt of said acid of formula I.

7. A pharmaceutical composition having antiinflammatory an analgesic activity, which comprises as the active ingredient an effective amount of a compound according to claim 1 and inert excipients.

8. A formulation according to claim 7, which is a composition suitable for oral administration.

9. A pharmaceutical composition according to claim 7 suitable for administration by the parenteral route.

10. The method of treating a living subject affected by pain and/or inflammation, which consists of administering to said living subject an effective amount of (2′,4′-difluoro-4-biphenyl)oxypropionic acid or a pharmaceutically acceptable salt thereof.

* * * * *